United States Patent
Sasaki et al.

(10) Patent No.: US 8,519,190 B2
(45) Date of Patent: Aug. 27, 2013

(54) CONCENTRATING METHOD, TREATING METHOD, CONCENTRATING SYSTEM AND TREATING SYSTEM FOR POLYISOCYANATE RESIDUES

(75) Inventors: Masaaki Sasaki, Kashima (JP); Tadashi Yoshida, Kamisu (JP); Shigetoshi Suzuki, Kamisu (JP)

(73) Assignee: Mitsui Chemicals, Inc., Minato-Ku, Tokyo (JP)

( * ) Notice: Subject to any disclaimer, the term of this patent is extended or adjusted under 35 U.S.C. 154(b) by 1327 days.

(21) Appl. No.: 11/988,677

(22) PCT Filed: Jul. 10, 2006

(86) PCT No.: PCT/JP2006/314119
§ 371 (c)(1), (2), (4) Date: Jan. 11, 2008

(87) PCT Pub. No.: WO2007/007887
PCT Pub. Date: Jan. 18, 2007

(65) Prior Publication Data
US 2009/0216042 A1    Aug. 27, 2009

(30) Foreign Application Priority Data
Jul. 12, 2005 (JP) ................... 2005-203221

(51) Int. Cl.
*C07C 263/20* (2006.01)
*C07C 265/14* (2006.01)

(52) U.S. Cl.
USPC .......................................... 564/393

(58) Field of Classification Search
None
See application file for complete search history.

(56) References Cited

U.S. PATENT DOCUMENTS

| | | |
|---|---|---|
| 3,128,310 A | 4/1964 | Koch |
| 3,410,888 A | 11/1968 | Hammond et al. |
| 4,032,574 A | 6/1977 | Keshi et al. |
| 4,123,601 A | 10/1978 | Kellum et al. |
| 4,137,266 A | 1/1979 | Cassata |
| 5,185,384 A | 2/1993 | Daussin et al. |
| 6,255,529 B1 | 7/2001 | Nagase et al. |
| 6,429,336 B2 | 8/2002 | Dai et al. |
| 6,462,230 B1 | 10/2002 | Nagase et al. |
| 6,630,517 B2 | 10/2003 | Nishida et al. |
| 6,673,960 B1 | 1/2004 | Schwarz et al. |
| 2003/0012710 A1 | 1/2003 | Nishida et al. |
| 2006/0011463 A1 | 1/2006 | Sohn et al. |

FOREIGN PATENT DOCUMENTS

| | | |
|---|---|---|
| EP | 0 976 719 A1 | 2/2000 |
| FR | 1.364.855 A | 5/1964 |
| GB | 1047101 | 11/1966 |
| GB | 1092019 | 11/1967 |
| GB | 1398975 | 6/1975 |
| JP | 49-095908 | 9/1974 |
| JP | 9-151270 A | 6/1997 |
| JP | 10-279539 A | 10/1998 |
| JP | 2002-173471 | 6/2002 |
| JP | 2002-518369 A | 6/2002 |
| JP | 2002-363336 | 12/2002 |
| WO | WO 99/65868 A1 | 12/1999 |
| WO | WO 2004/056761 A1 | 7/2004 |

OTHER PUBLICATIONS

Results obtained using BP calculator, 2005.*
Notice of Allowance issued in corresponding Japanese Patent Application No. 2005-203222 dated Mar. 8, 2011.

* cited by examiner

*Primary Examiner* — Yevegeny Valenrod
(74) *Attorney, Agent, or Firm* — Buchanan Ingersoll & Rooney PC

(57) ABSTRACT

A concentrating method and a concentrating system for concentrating polyisocyanate residues that that can effectively concentrate polyisocyanate residues from crude polyisocyanate comprising polyisocyanate and polyisocyanate residues in a short time and can also suppress increase in viscosity to provide stable transport of the residues and prevent blockage of the transport line, and a treating method and a treating system for decomposing the concentrated components to polyamine.

The polyisocyanate residues are first heated on the boil by the distiller to be concentrated to a midterm concentrating rate, and then, the polyisocyanate residues are concentrated to the final concentrating rate by evaporation using a evaporator. This can allow the polyisocyanate residues to be decomposed to polyamine to be recovered by setting a Cl content of a high boiling point distillate fraction concentrated to be not more than 2 weight % and then putting the high boiling point distillate fraction into contact with high temperature and high pressure water to be hydrolyzed by the decomposing apparatus.

5 Claims, 1 Drawing Sheet

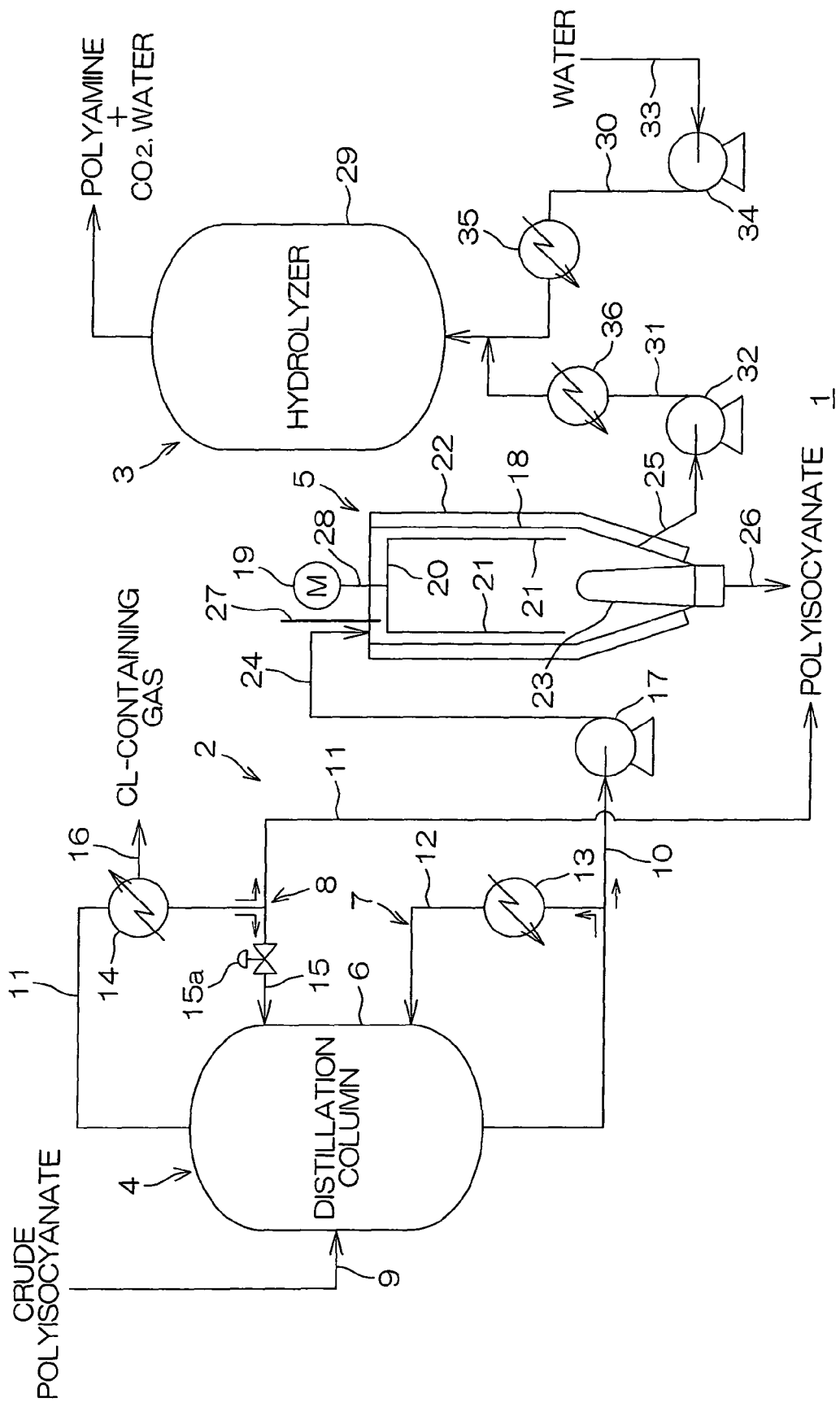

CONCENTRATING METHOD, TREATING METHOD, CONCENTRATING SYSTEM AND TREATING SYSTEM FOR POLYISOCYANATE RESIDUES

TECHNICAL FIELD

The present invention relates to a concentrating method, treating method, concentrating system and treating system for polyisocyanate residues. More particularly, the present invention relates to a concentrating method and a concentrating system for concentrating polyisocyanate residues from crude polyisocyanate comprising polyisocyanate and polyisocyanate residues, and to a treating method and a treating system for decomposing the obtained concentrated components to polyamine.

BACKGROUND ART

Polyisocyanate, used as a raw material of polyurethane, is industrially produced, for example, by allowing polyamine to react with carbonyl chloride for isocyanate reaction.

In such a producing of polyisocyanate, after completion of the isocyanate reaction, high-molecular-weight polyisocyanate, which is byproducts produced as residues are heated and concentrated by distillation operation thereby to be separated from the crude polyisocyanate (cf. Patent Document 1, for example).

Meanwhile, it is known that the crude polyisocyanate containing polyisocyanate residues is undesirably subject to thermal polymerization, such as dimer reaction, trimer reaction, and carbodiimide reaction, by the application of heat. In the distillation operation, while polyisocyanate is distilled together with a Cl-containing gas secondarily produced, such as hydrogen chloride and carbonyl chloride, the polyisocyanate residues are concentrated. While being concentrated, the polyisocyanate residues are thermally polymerized as described above and increased in viscosity, to cause unstable transport of the residues and further a possible blockage of the transport line.

Meanwhile, an evaporation operation using a thin film evaporator is known as a refining technique for an organic compound susceptible to thermal polymerization and is widely used industrially.

Further, in recent years, there have been proposed methods wherein the residues produced is continuously fed to a reactor vessel in its liquid state or solution state, while also high-temperature and high-pressure water is continuously fed to the reaction vessel, with temperature of the reaction vessel controlled to 190-300° C., whereby the residues are decomposed to polyamine and the polyamine is recovered (cf. Patent Document 2, for example).

[Patent Document 1] Japanese Unexamined Patent Publication No. 2002-518369.

[Patent Document 2] Japanese Unexamined Patent Publication No. Hei 10-279539.

DISCLOSURE OF THE INVENTION

Problem to be Solved by the invention

When the high-molecular-weight polyisocyanate, produced as the residues are concentrated from the crude polyisocyanate obtained by the evaporation operation using a thin film evaporator and the like, the time required for the concentration can be made shorter than when concentrated by the distillation operation. As a result of this, a heat history of the residues can be reduced, and thus the thermal polymerization thereof can be suppressed.

However, in the evaporation operation, the Cl-containing gas in the residues, such as hydrogen chloride and carbonyl chloride, cannot be removed sufficiently. As a result, due to the remaining Cl-containing gas, such as hydrogen chloride and carbonyl chloride, the residues are polymerized and increased in viscosity during transport of the residues and at locations where the residues are temporarily stayed, then causing unstable transport of the residues and further a possible blockage of the transport line.

It is an object of the present invention to provide a concentrating method and system for concentrating polyisocyanate residues that can effectively concentrate polyisocyanate residues from crude polyisocyanate comprising polyisocyanate and polyisocyanate residues in a short time and can also suppress increase in viscosity to provide stable transport of the residues and prevent blockage of the transport line. It is another object of the present invention to provide a treating method and system for decomposing the obtained concentrated components to polyamine.

Means for Solving the Problem

The present invention provides a concentrating method for polyisocyanate residues from crude polyisocyanate containing polyisocyanate and polyisocyanate residues, which comprises a first concentrating process of concentrating the polyisocyanate residues from the crude polyisocyanate to a midterm concentrating rate on the way to a final concentrating rate by heating the crude polyisocyanate on the boil, to obtain a first concentrated component, and a second concentrating process of concentrating the first concentrated component concentrated in the first concentrating process to the final concentrating rate by evaporation, to obtain a second concentrated component.

According to this concentrating method, the crude polyisocyanate is heated on the boil in the first concentrating process. This can provide the treating time required for not only the polyisocyanate but Cl-containing gas secondarily produced, such as hydrogen chloride and carbonyl chloride, to be distilled while the polyisocyanate residues are concentrated. Besides, in the first concentrating process, the crude polyisocyanate is only concentrated to the midterm concentrating rate on the way to the final concentrating rate. Hence, the thermal polymerization of the crude polyisocyanate can be suppressed. The thermal polymerization of the crude polyisocyanate includes reaction of polyisocyanate with polyisocyanate residues. In the case where this reaction is a second-order reaction, when polyisocyanate and polyisocyanate residues are equal in amount, polymerization is promoted most. Further, as the polyisocyanate residues are concentrated, a viscosity of the concentrated solution is increased significantly. When the treating time required for the Cl-containing gas secondarily produced, such as hydrogen chloride and carbonyl chloride, to be distilled together with polyisocyanate is given in the state where the polyisocyanate residues are concentrated to the final concentrating rate, in addition to the thermal polymerization of polyisocyanage and polyisocyanate residues, temperature of a heating medium rises due to contamination of a reboiler, reduction in coefficient of heat transfer, and increase in boiling point caused by increase of the polyisocyanate residues. This may cause the blockage of the reboiler and a transport line.

Then, in the second concentrating process, the first concentrated component obtained in the first concentrating process is concentrated to the final concentrating rate by evaporation. Since the Cl-containing gas, such as hydrogen chloride and carbonyl chloride, is already removed from the first concentrated component in the first concentrating process, increase in viscosity of the polyisocyanate residues caused by the remaining Cl-containing gas, such as hydrogen chloride and carbonyl chloride, can be suppressed. Besides, as the polyisocyanate residues are evaporated, the time required for the concentration can be shorten so that the heat history can be reduced and thus the thermal polymerization thereof can be suppressed.

As a result of this, in this method, the polyisocyanate residues can effectively be concentrated from the crude polyisocyanate in a short time. Besides, by suppressing the increase in viscosity, a stable transport of the polyisocyanate residues can be provided, while a possible blockage of the transport line can be prevented.

In the concentrating method for polyisocyanate residues of the present invention, it is preferable that a concentrating rate of the first concentrated component is set so that a concentrating rate of the polyisocyanate is 95-60 weight % per 100 weight % first concentrated component, and a concentrating rate of the polyisocyanate residues is 5-40 weight % per 100 weight % first concentrated component, and that a concentrating rate of the second concentrated component is set so that a concentrating rate of the polyisocyanate is 10-59 weight % per 100 weight % second concentrated component, and a concentrating rate of the polyisocyanate residues is 90-41 weight % per 100 weight % second concentrated component.

In the concentrating method for polyisocyanate residues of the present invention, it is preferable that the crude polyisocyanate is heated at 155-190° C. in the first concentrating process.

In the concentrating method for polyisocyanate residues of the present invention, it is preferable that the first concentrated component is evaporated using a thin film evaporator in the second concentrating process.

In the concentrating method for polyisocyanate residues of the present invention, it is preferable that a Cl content of the second concentrated component is not more than 2 weight %.

When the Cl content of the second concentrated component is not more than 2 weight %, the increase in viscosity of the residues can be prevented effectively.

The present invention provides a treating method for polyisocyanate residues wherein a second concentrated component obtained by the concentrating method for concentrating polyisocyanate residues described above is put in contact with high temperature and high pressure water, whereby it is decomposed to polyamine.

The present invention provides a treating method for polyisocyanate residues wherein crude polyisocyanate comprising polyisocyanate and polyisocyanate residues and having a Cl content of not more than 2 weight % is put in contact with high temperature and high pressure water, whereby it is decomposed to polyamine.

According to these treating methods, since the second concentrated component having a Cl content of not more than 2 weight % is decomposed to polyamine by being put in contact with high temperature and high pressure water, polyamine can be recovered at a high recovering rate.

The present invention provides a concentrating system for polyisocyanate residues, which comprises a distiller for concentrating polyisocyanate residues from crude polyisocyanate comprising polyisocyanate and polyisocyanate residues to a midterm concentrating rate on the way to a final concentrating rate by heating the crude polyisocyanate on the boil, to obtain a first concentrated component, and an evaporator, connected to the distiller, for concentrating the first concentrated component concentrated in the distiller to the final concentrating rate by evaporation, to obtain a second concentrated component.

According to this concentrating system, the crude polyisocyanate is heated on the boil in the distiller, first. This can provide the treating time required for not only the polyisocyanate but the Cl-containing gas secondarily produced, such as hydrogen chloride and carbonyl chloride, to be distilled while the polyisocyanate residues are concentrated. Besides, in the distiller, the crude polyisocyanate is only concentrated to the midterm concentrating rate on the way to the final concentrating rate. Hence, the thermal polymerization of the crude polyisocyanate can be suppressed. Then, in the evaporator, the first concentrated component obtained in the distiller is concentrated to the final concentrating rate by evaporation. Since the Cl-containing gas, such as hydrogen chloride and carbonyl chloride, is already removed in the distiller, increase in viscosity of the polyisocyanate residues caused by the remaining Cl-containing gas, such as hydrogen chloride and carbonyl chloride, can be suppressed. Besides, as the polyisocyanate residues are evaporated, the time required for the concentration can be shorten so that the heat history can be reduced and thus the thermal polymerization can be suppressed.

As a result of this, in this concentrating system, the polyisocyanate residues can effectively be concentrated from the crude polyisocyanate in a short time. Besides, by suppressing the increase in viscosity, a stable transport of the polyisocyanate residues can be provided, and a possible blockage of the transport line can be prevented.

In the concentrating system for polyisocyanate residues of the present invention, it is preferable that the evaporator used for obtaining the second concentrated component is a thin film evaporator.

The present invention provides a treating system for polyisocyanate residues, which comprises the above-described concentrating system for the polyisocyanate residues, and a decomposing apparatus for putting the second concentrated component obtained by the concentrating system in contact with high temperature and high pressure water, so that it is decomposed to polyamine.

According to this treating system, since the second concentrated component is put in contact with high temperature and high pressure water, whereby the second concentrated component is decomposed to polyamine, polyamine can be recovered at a high recovering rate.

Effect of the Invention

According to the concentrating method and system for polyisocyanate residues of the present invention, polyisocyanate residues can be effectively concentrated from crude polyisocyanate in a short time. Besides, by suppressing the increase in viscosity, a stable transport of the polyisocyanate residues can be achieved, and a possible blockage of the transport line can be prevented.

Further, according to the treating method and system for the polyisocyanate residues of the present invention, polyamine can be recovered at a high recovering rate.

BRIEF DESCRIPTION OF THE DRAWINGS

FIG. 1 is a schematic block diagram showing an embodiment of a treating system for polyisocyanate residues of the present invention.

EXPLANATION OF NUMERALS

1: Treating system
2: Concentrating apparatus

3: Decomposing apparatus
4: Distiller
5: Evaporator

Embodiment of the Invention

FIG. 1 is a schematic block diagram showing an embodiment of a treating system for polyisocyanate residues of the present invention.

In FIG. 1, the treating system 1 includes a concentrating apparatus 2, and a decomposing apparatus 3 connected to the concentrating apparatus 2. This treating system 1 is equipped in a producing plant for polyisocyanate, for the purpose of concentrating polyisocyanate residues (distillation residues) from crude polyisocyanate (unrefined polyisocyanate) produced in a subsequent process of a producing process of polyisocyanate and then decomposing the concentrated composition to polyamine by high temperature and high pressure water.

The concentrating apparatus 2 includes a distiller 4 and an evaporator 5 connected to the distiller 4. The distiller 4 is provided with a distillation column 6, a heating unit (reboiler) 7, and a cooling unit 8.

The distillation column 6 may comprise either a simple distillation column, or a plate column or a packed column designed to have required theoretical stages. A feed pipe 9 for feeding crude polyisocyanate is connected to a vertically intermediate portion of the distillation column 6.

The crude polyisocyanate includes, in addition to polyisocyanate produced by reaction of carbonyl chloride with polyamine in the producing process, polyisocyanate residues, and Cl-containing gas such as hydrogen chloride and carbonyl chloride, and a reaction compound of polyisocyanate with Cl-containing gas, such as hydrogen chloride and carbonyl chloride, which are secondarily produced by the same reaction. The crude polyisocyanate is fed to the feed pipe 9 after reaction solvent is removed from the polyisocyanate produced in the producing process in a desolvating process.

Polyisocyanates that depend on polyisocyanate produced by a producing plant include, for example, polymethylenepolyphenylene polyisocyanate (MDI), tolylene diisocyanate (TDI), xylylene diisocyanate (XDI), tetramethylxylylene diisocyanate (TMXDI), bis(isocyanatomethyl) norbornane (NBDI), 3-isocyanatomethyl-3,5,5-trimethylcyclohexyl isocyanate (IPDI), 4,4'-methylenebis(cyclohexylisocyanate) ($H_{12}$MDI), bis(isocyanatomethyl)cyclohexane ($H_6$XDI), and hexamethylene diisocyanate (HDI).

Polyisocyanate residues, which is content of tar containing primarily of high-molecular-weight polyisocyanates, include dimer, trimer, carbodiimide, uretodion, uretoneimine, dimers containing isocyanurate groups and multimeric complexes of at least trimers containing isocyanurate groups, of polyisocyanate.

The crude polyisocyanate has a polyisocyanate content of e.g. 99-80 weight % and polyisocyanate residues contents of e.g. 1-20 weight % per 100 weight % crude polyisocyanate. The crude polyisocyanate has a content of Cl-containing gas, such as hydrogen chloride and carbonyl chloride, of 0.05-5 weight % in terms of a Cl content (which is determined by total Cl measurement pursuant to JIS K 1556, provided, however, that when the crude polyisocyanate comprises a solvent containing a Cl group, a Cl content resulting from the solvent is deduced from the total Cl measurement value. The same applies to the following measurement). It is to be noted that the solvent need not necessarily be removed completely from the crude polyisocyanate, within the scope of the effect of the present invention not being decreased. The crude polyisocyanate may contain the solvent to the extent equal in amount to the crude polyisocyanate.

An upstream end of a bottoms take-out pipe 10, through which bottoms containing the polyisocyanate residues are taken out from the crude polyisocyanate, is connected to a bottom of the distillation column 6. An upstream end of a distillate solution take-out pipe 11, through which a distillate solution containing primarily polyisocyanate is taken out from the crude polyisocyanate, is connected to a top of the distillation column 6.

A heating unit 7 includes the bottoms take-out pipe 10, a heat-circulation line 12 whose upstream end is connected to the bottoms take-out pipe 10 and whose downstream end is connected to the bottom of the distillation column 6, and a heater 13 interposed in the heat-circulation line 12. The heater 13 comprises a heat exchanger to which heating medium is supplied. In the heating unit 7, a heating temperature of the heater 13 is adjusted to e.g. 155-190° C. to which the bottoms to circulate along the heat-circulation line 12 is heated. Alternatively, the heating unit 7 may comprise a tank or an agitator tank having a heating means, such as a jacket or a coil to which the heating medium is supplied. In this arrangement, the feed pipe 9 to which the crude polyisocyanate is fed may be connected to the tank or the agitator tank having such a heating means.

A cooling unit 8 includes the distillate solution take-out pipe 11, and a cooler 14 interposed in that pipe 11. If necessary, a cool-circulation line 15 whose upstream end is connected to the distillate solution take-out pipe 11 at a location downstream from the cooler 14 and intermediate the distillate solution take-out pipe 11 and whose downstream end is connected to the top of the distillation column 6 may be provided. A flow regulating valve 15a for regulating a flow of the distillate solution back to the top of the distillation column 6 is interposed in the cool-circulation line 15.

The cooler 14 comprises a heat exchanger to which cooling medium is supplied. A vacuum line 16 is connected to the cooler 14, and an ejector or a vacuum pump, not shown, is connected to the vacuum line 16, to reduce the pressure in the distillate solution take-out pipe 11 and in turn the pressure in the distillation column 6. In the cooling unit 8, the cooling temperature of the cooler 14 is adjusted to e.g. 30-140° C. to cool the distillate solution.

In this distiller 4, the crude polyisocyanate is fed from the feed pipe 9 to the distillation column 6 or the tank or the agitator tank having the heating means of the heating unit 7. An inner pressure of the distillation column 6 is reduced to 0.05-30 kPa to boil polyisocyanate. Besides, the distillation column 6 is heated at the bottom at e.g. 155-190° C., or preferably 160-190° C., by the heating unit 7. As a result, polyisocyanate contained in the crude polyisocyanate is heated while being boiled at the bottom of the distillation column 6. On the other hand, the distillation column 6 is cooled down at the top thereof by the cooling unit 8, to cool down the boiling and rising polyisocyanate in temperature to e.g. 30-140° C., or preferably 40-120° C. As a result, the polyisocyanate is condensed and then taken out as the distillate solution.

Thus, the polyisocyanate residues are concentrated from the crude polyisocyanate at the bottom of distillation column 6. Then, the concentrated components (first concentrated components) are circulated as bottoms along the heat-circulation line 12, while a part of the bottoms is continuously let out from the bottoms take-out pipe 10 (first concentrating process). At the top of distillation column 6, polyisocyanate is taken out from the crude polyisocyanate as a distillate solution and is continuously distillated from the distillate solution take-out pipe 11.

The Cl-containing gas secondarily produced, such as hydrogen chloride and carbonyl chloride, is entrained with the boiling polyisocyanate, then is flown from the top of the distillation column 6 into the distillate solution take-out pipe 11, and then is drained through the vacuum line 16 of the cooler 14.

The time required for the bottoms to be treated in the distillation column 6 for the crude polyisocyanate (which is determined by dividing total hold up time of the reboiler and of the bottom of the distillation column by a flow rate of the bottoms, which is sometimes called the residence time of the reboiler) is set to be in the range of e.g. 0.5-8 hours, or preferably 1-4 hours. A concentrating rate (midterm concentrating rate) of the polyisocyanate in the bottoms is set to be e.g. 95-60 weight %, or preferably 90-60 weight %, per 100 weight % bottoms, and a concentrating rate (midterm concentrating rate) of the polyisocyanate residues in the bottoms is set to be e.g. 5-40 weight %, or preferably 10-40 weight %, per 100 weight % bottoms.

A first liquid sending pump 17 is connected to the downstream end of the bottoms take-out pipe 10, so that the bottoms are pressure-transported to the evaporator 5 by the first liquid sending pump 17.

After the distillate solution from the distillate solution take-out pipe 11 together with the distillate solution from a lower outlet pipe 26 mentioned later is rectified in a rectifying column and the like, they are taken out as a polyisocyanate product.

The evaporator 5 comprises a thin film evaporator, including a casing 18, a motor 19, a rotor 20, a wiper 21, a jacket 22, and an internal condenser 23, for example. Although the thin film evaporator of internal condenser type is shown in FIG. 1, this type of evaporator is not exclusive. Evaporators that may be used include a thin film evaporator of external condenser type, a falling film evaporator of multi-tubular type, a climbing film evaporator and a wiped film evaporator.

The casing 18 is formed in a vertically elongate cylindrical form with its lower part formed in a funnel shape. The casing 18 is formed so that its interior space is an airtight container allowing to reduce the pressure.

A downstream end of an upper inlet pipe 24 for letting the bottoms flow into the casing 18 is connected to an upper wall of the casing 18. An upstream end of the upper inlet pipe 24 is connected to the first liquid sending pump 17. An upstream end of a lateral outlet pipe 25 for distilling a high boiling point distillate fraction is connected to a lower side wall of the casing 18. A downstream end of the lateral outlet pipe 25 is connected to a second liquid sending pump 32 for pressure-transporting the high boiling point distillate fraction to the decomposing apparatus 3. The lower outlet pipe 26 for distilling a low boiling point distillate fraction is connected to a bottom wall of the casing 18. A vacuum suction pipe 27 to reduce the pressure of the interior of the casing 18 is connected to the upper wall of the casing 18.

The motor 19 is disposed above the casing 18, and a drive shaft 28 of the motor 19 extends along a central axis of the casing 18, extending through the upper wall of the casing 18.

The rotor 20 is connected to a lower end of the drive shaft 28 and is arranged radially around the drive shaft 28 to extend radially outwardly from the lower end of the drive shaft 28. The rotor 20 is disposed so that its radially outer end is disposed opposite to and closely spaced from an inner circumferential surface of the side wall of the casing 18.

The wiper 21 is arranged to extend along the vertical direction from the radially outer end of the rotor 20. The wiper 21 is disposed vertically opposite to and closely spaced from the inner circumferential surface of the side wall of the casing 18.

The jacket 22 is arranged outside of the side wall of the casing 18 to heat the interior of the casing 18. The jacket 22 is arranged along a longitudinal direction (a vertical direction) of the casing 18, to cover the outer circumferential surface of the side wall of the casing 18. The heating medium is fed to the interior of the jacket 22.

The internal condenser 23 is disposed on a bottom wall of the casing 18, comprising a heat exchanger through which the cooling medium is circulated. The internal condenser 23 communicates with the lower outlet pipe 26.

The bottoms pressure-transported from the first liquid sending pump 17 flow into the casing 18 from the upper inlet pipe 24. In the casing 18, the drive shaft 28 is rotated by the drive of the motor 11, to rotate the rotor 20 around the drive shaft 28, and the wiper 21 is moved circumferentially with being closely spaced from the inner circumferential surface of the side wall of the casing 18. The casing 18 is reduced in inner pressure to 0.01-20 kPa by the suction of the vacuum suction pipe 27 and also is heated to 80-230° C. by the jacket 22.

The bottoms flowing into the casing 18 from the upper inlet pipe 24 is moved by a centrifugal force of the wiper 21 moved in the circumferential direction, so that they are formed in a liquid thin film in a space closely spaced between the inner circumferential surface of the side wall of the casing 18 and the wiper 21. Then, the polyisocyanate contained in the liquid thin film is evaporated by heating from the jacket 22 and, then, is concentrated by the internal condenser 23. Thereafter, the polyisocyanate thus concentrated is drained through the lower outlet pipe 26 as the low boiling point distillate fraction. On the other hand, the polyisocyanate residues contained in the liquid thin film is concentrated as it is, without being evaporated from the liquid thin film. Thereafter, the polyisocyanate residues thus concentrated is drained through the lateral outlet pipe 25 as the high boiling point distillate fraction (second concentrated component). This is a second concentrating process.

A concentrating rate (final concentrating rate) of the polyisocyanate in the high boiling point distillate fraction is set to be e.g. 10-59 weight %, or preferably 20-55 weight %, per 100 weight % high boiling point distillate fraction, and a concentrating rate (final concentrating rate) of the polyisocyanate residues in the high boiling point distillate fraction is set to be e.g. 90-41 weight %, or preferably 80-45 weight %, per 100 weight % high boiling point distillate fraction. Further, the high boiling point distillate fraction has a hydrogen chloride content of not more than 2 weight %, or preferably not more than 1.5 weight %, in terms of a Cl content.

In this concentrating apparatus 2, the crude polyisocyanate is first heated on the boil in the distiller 4, as described above. This can provide the treating time required for not only the polyisocyanate but the Cl-containing gas secondarily produced, such as hydrogen chloride and carbonyl chloride, to be distilled while the polyisocyanate residues are concentrated as the bottoms. Besides, in the distiller 4, the crude polyisocyanate is only concentrated to the midterm concentrating rate on the way to the final concentrating rate. Hence, the thermal polymerization of the crude polyisocyanate can be suppressed. Then, in the evaporator 5, the bottoms obtained by the distiller 4 is concentrated to the final concentrating rate by the thin film evaporation. Since the Cl-containing gas, such as hydrogen chloride and carbonyl chloride, is already removed from the bottoms in the distiller 4, increase in viscosity of the polyisocyanate residues caused by the remaining Cl-containing gas, such as hydrogen chloride and carbonyl chloride, and the reactant thereof can be suppressed. Besides, as the polyisocyanate residues are evaporated by the thin film evaporation, the time required for the concentration can be shorten so that the heat history can be reduced and thus the thermal polymerization can be suppressed.

As a result of this, in the concentrating apparatus 2, the polyisocyanate residues can effectively be concentrated from the crude polyisocyanate in a short time. Besides, by suppressing the increase in viscosity, a stable transport of the polyisocyanate residues can be achieved, and a possible blockage of the transport line (the lateral outlet pipe 25 and a residual feed pipe 31 mentioned later) can be prevented.

TABLE 1 shows a relationship between a Cl content of bottoms and increase in viscosity when crude polyisocyanate is concentrated by varying heat treatment temperature (bottom temperature) and treating time (bottom treating time) in the distiller 4, to produce tolylene diisocyanate. It can be seen from TABLE 1 that when the Cl content of the bottoms is not less than 2 weight %, the increase in viscosity of the residues can be suppressed.

Although the embodiment wherein the distiller 4 and the evaporator 5 both have a single-stage structure has been illustrated above, they may properly be modified to have a multi-stage structure, depending on intended purposes and applications. Further, the crude polyisocyanate may be concentrated in such a manner that it is first concentrated to a midterm concentration using the thin film evaporator and then to a predetermined final concentration of the polyamine residues using the distiller 4 and the evaporator 5 in the concentrating apparatus 2 of the present invention.

The decomposing apparatus 3 includes a hydrolyzer 29, a water feed pipe 30 connected to the hydrolyzer 29, and a residual feed pipe 31 connected to the water feed pipe 30.

The hydrolyzer 29 is a hydrolyzing reactor for the polyisocyanate residues to be hydrolyzed to polyamine by contact of the polyisocyanate residues with high temperature and high pressure water. It comprises a heat-resistant and pressure-resistant container whose temperature and pressure can be controlled.

The water feed pipe 30 is a water feed line for feeding high temperature and high pressure water to the hydrolyzer 29. It comprises a heat-resistant and pressure-resistant pipe whose downstream end is connected to the hydrolyzer 29 and whose upstream end is connected to a water pressure-feed pump 34 for pressure-transporting the high temperature and high pressure water to the hydrolyzer 29. A feed water line 33 for feeding industrial water (process water) is connected to the water pressure-feed pump 34. A water heater 35 is interposed in the water feed pipe 30.

The residual feed pipe 31 is a residual feed line for feeding the high boiling point distillate fraction to the hydrolyzer 29, together with the high temperature and high pressure water. It comprises a heat-resistant and pressure-resistant pipe whose downstream end is connected to a midstream of the water feed pipe 30 at a location on the downstream side of the water heater 35 and whose upstream end is connected to the second liquid sending pump 32.

A residual heater 36 is interposed in the residual feed pipe 31.

In the decomposing apparatus 1, the high boiling point distillate fraction is pressure-transported through the residual feed pipe 31 toward the water feed pipe 30 by the second liquid sending pump 32 and is heated to e.g. 120-180° C. by the residual heater 36. As a result, the high boiling point distillate fraction flows into the water feed pipe 30 in the state of being increased in pressure to a feeding pressure of e.g. 5-30 MPa and heated to a feeding temperature of 120-180° C.

On the other hand, the process water flowing into the water feed pipe 30 from the water feed line is pressure-transported through the water feed pipe 30 toward the hydrolyzer 29 by the water pressure-feed pump 34 and is heated to e.g. 190-300° C. by the water heater 35. As a result, the process water becomes a high temperature and high pressure water by being increased in pressure to 5-30 MPa and also heated to 190-300° C., flowing into the hydrolyzer 29 together with the polyisocyanate residues fed from the residue feed pipe 31.

In the hydrolyzer 29, for example, an internal temperature (decomposing temperature) of the hydrolyzer 29 is controlled to 190-300° C. and an internal pressure (decomposing pressure) of the same is controlled to 5-30 MPa. Further, a hydrolytic ratio (a weight ratio of high temperature and high pressure water to polyisocyanate residues) is controlled to e.g. 0.5-5 under control of the second liquid sending pump 32 and the water pressure-feed pump 34.

As a result of this, in the hydrolyzer 29, the high boiling point distillate fraction is hydrolyzed by the high temperature and high pressure water to produce corresponding polyamine as a decomposition product, while carbon dioxide, water, etc. are produced secondarily.

Polyamines include, for example, polymethylenepolyphenylene polyamine (MDA) corresponding to polymethylenepolyphenylene polyisocyanate (MDI), tolylene diamine (TDA) corresponding to tolylene diisocyanate (TDI), xylylene diamine (XDA) corresponding to xylylene diisocyanate (XDI), tetramethylxylylene diamine (TMXDA) corresponding to tetramethylxylylene diisocyanate (TMXDI), bis (aminomethyl)norbornane (NBDA) corresponding to bis (isocyanatomethyl)norbornane (NBDI), 3-aminomethyl-3,5, 5-trimethylcyclohexyl amine (IPDA) corresponding to 3-isocyanatomethyl-3,5,5-trimethylcyclohexyl isocyanate (IPDI), 4,4'-methylenebis(cyclohexylamine) ($H_{12}$MDA) corresponding to 4,4'-methylenebis(cyclohexyliсocyanate) ($H_{12}$MDI), bis(aminomethyl)cyclohexane ($H_6$XDA) corresponding to bis(isocyanatomethyl)cyclohexane ($H_6$XDI), and hexamethylene diamine (HDA) corresponding to hexamethylene diisocyanate (HDI).

Then, after the decomposition product drained through the hydrolyzer 29 is reduced in pressure to the atmospheric pressure, it is separated to each in a dehydrating column, not shown, so that polyamine is recovered. The polyamine thus recovered is reused as polyamine of raw material in the producing process for polyisocyanate.

In the decomposition of high boiling point distillate fraction to polyamine in such decomposing apparatus 3, as long as a Cl content of the high boiling point distillation fraction is not more than 2 weight %, corrosion in the decomposing apparatus 3 can be reduced, while also polyamine can be recovered at a high recovering rate.

TABLE 1 shows a recovering rate of polyamine when the various bottoms cited above are decomposed by the decomposing apparatus 3 (decomposing temperature of 250° C., decomposing pressure of 12 MPa, and hydrolytic ratio of 2.5). It can be seen from TABLE 1 that as long as a Cl content of the bottoms is not more than 2 weight %, polyamine can be recovered at a high recovering rate.

TABLE 1

| | Bottom No. | | | | | |
|---|---|---|---|---|---|---|
| | 1 | 2 | 3 | 4 | 5 | Compara. 1 |
| Temperature of Bottom in Distiller (° C.) | 170 | 170 | 155 | 140 | 180 | ※1 |
| Treating Time for Bottom in Distiller (min.) | 60 | 180 | 60 | 60 | 120 | ※1 |

TABLE 1-continued

| | Bottom No. | | | | | |
|---|---|---|---|---|---|---|
| | 1 | 2 | 3 | 4 | 5 | Compara. 1 |
| Cl content of Bottoms (wt. %) | 1.3 | 1.0 | 2.3 | 3.0 | 0.9 | 3.4 |
| TDI Content in Bottoms (wt. %) | 40 | 40 | 40 | 40 | 40 | 40 |
| Initial Viscosity of Bottoms (mPas) ※2 | 190 | 200 | 130 | 55 | 440 | 30 |
| Viscosity of Bottoms 2 hrs. later (mPas) ※2 | 400 | 350 | 1050 | >5000 | 570 | >10000 (1 Hr) |
| Recovering rate of TDA (%) ※3 | 93 | 95 | 85 | 79 | 95 | |

TDI: Tolylene diisocyanate
TDA: Tolylene diamine
※1: Single stage concentration using a thin film evaporator
※2 Viscosity is a measured value measured at 140° C.
※3 TDA recovering rate = (Amount (g) of TDA recovered)/(theoretical amount (g) of TDA recovery when bottoms are all TDI)

In TABLE 1, a TDI content is measured in the following manner.

After 50 g of crude TDI or a concentrated solution thereof (TDI+residues TDI) is put in a 200 ml pear-shaped flask, a distillation column, a cooler, a nitrogen gas inlet pipe, and a receiver are connected to the flask. Then, the pear-shaped flask is heated under vacuum of 1 kPa, using an oil bath, so that TDI is distilled at 100-250° C. A distillate solution and a residue in the pear-shaped flask are measured by weight and an amount of a solvent is determined by an analysis of the distillate solution using a gas chromatograph. Then, the TDI content is calculated from the following formula.

TDI content (weight %)=(Weight (g) of distillate solution−Amount (g) of solvent in distillate solution)/(Weight (g) of concentrate distillate solution−Amount (g) of solvent in distillate solution)×100

While the illustrative embodiments of the present invention are provided in the above description, such is for illustrative purpose only and it is not to be construed restrictively. Modification and variation of the present invention that will be obvious to those skilled in the art is to be covered by the following claims.

INDUSTRIAL APPLICABILITY

The concentrating method, treating method, concentration system and treating system for polyisocyanate residues of the present invention can be suitably used for producing polyisocyanate industrially.

The invention claimed is:

1. A concentrating method for tolylene diisocyanate residues from crude tolylene diisocyanate comprising tolylene diisocyanate and tolylene diisocyanate residues, which comprises:

a first concentrating process of concentrating the tolylene diisocyanate residues from the crude tolylene diisocyanate to a midterm concentrating rate on the way to a final concentrating rate by heating the crude tolylene diisocyanate which is on the boil, to obtain a first concentrated component, using a distillation column within the range of 155-190° C. at 0.05-30 kPa, and a second concentrating process of concentrating the first concentrated component concentrated in the first concentrating process to the final concentrating rate by evaporation, to obtain a second concentrated component.

2. The concentrating method for tolylene diisocyanate residues according to claim 1, wherein a concentrating rate of the first concentrated component is set so that a concentrating rate of the tolylene diisocyanate is 95-60 weight % per 100 weight % of the first concentrated component, and a concentrating rate of the tolylene diisocyanate residues is 5-40 weight % per 100 weight % of the first concentrated component, and a concentrating rate of the second concentrated component is set so that a concentrating rate of the tolylene diisocyanate is 10-59 weight % per 100weight % of the second concentrated component, and a concentrating rate of the tolylene diisocyanate residues is 90-41 weight % per 100 weight % of the second concentrated component.

3. The concentrating method for tolylene diisocyanate residues according to claim 1, wherein the first concentrated component is evaporated using a thin film evaporator in the second concentrating process.

4. The concentrating method for tolylene diisocyanate residues according to claim 1, wherein a Cl content of the second concentrated component is not more than 2 weight %.

5. A treating method for tolylene diisocyanate residues wherein a second concentrated component obtained by a concentrating method for concentrating tolylene diisocyanate residues from crude tolylene diisocyanate comprising tolylene diisocyanate and tolylene diisocyanate residues is put in contact with high temperature and high pressure water and is decomposed to tolylene diamine, the concentrating method comprising a first concentrating process of concentrating the tolylene diisocyanate residues from the crude tolylene diisocyanate to a midterm concentrating rate on the way to a final concentrating rate by heating the crude tolylene diisocyanate on the boil to obtain a first concentrated component using a distillation column within the range of 155-190° C. at 0.05-30 kPa, and a second concentrating process of concentrating the first concentrated component concentrated in the first concentrating process to the final concentrating rate by evaporation to obtain a second concentrated component, a Cl content of the second concentrated component being not more than 2weight %.

* * * * *